Figure 1:
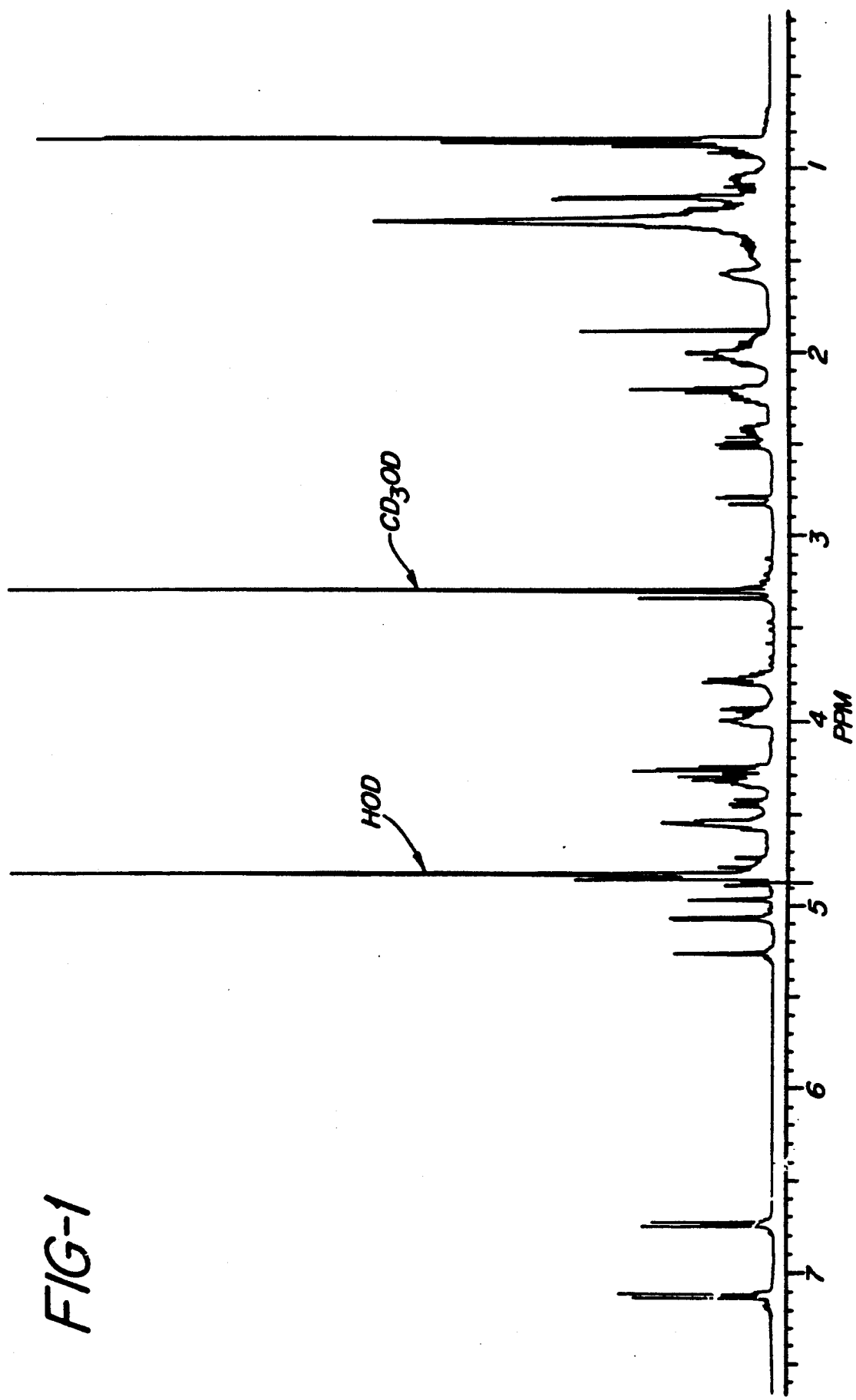

United States Patent [19]

Giacobbe et al.

[11] Patent Number: 5,021,341
[45] Date of Patent: Jun. 4, 1991

[54] ANTIBIOTIC AGENT PRODUCED BY THE CULTIVATION OF ZALERION MICROORGANISM IN THE PRESENCE OF MANNITOL

[75] Inventors: Robert A. Giacobbe, Lavallette; Jan S. Tkacz, Piscataway; Prakash S. Masurekar, Warren, all of N.J.; Louis Kaplan, New City, N.Y.; Margaret S. Sosa, Elizabeth, N.J.

[73] Assignee: Merck & Co., Inc., Rahway, N.J.

[21] Appl. No.: 492,026

[22] Filed: Mar. 12, 1990

[51] Int. Cl.⁵ .................. C12P 21/04; C12N 1/00; C12N 1/14; C12N 1/32
[52] U.S. Cl. .................. 435/71.1; 435/71.3; 435/119; 435/247; 435/254; 435/911
[58] Field of Search .............. 435/71.1, 71.3, 119, 435/911; 425/254, 247

[56] References Cited

U.S. PATENT DOCUMENTS

| | | |
|---|---|---|
| 3,978,210 | 8/1976 | Mizuno et al. . |
| 4,024,245 | 5/1977 | Hoehn et al. . |
| 4,024,246 | 5/1977 | Higgens et al. . |
| 4,173,629 | 11/1979 | Dreyfuss et al. . |
| 4,287,120 | 9/1981 | Abbott et al. . |
| 4,288,549 | 9/1981 | Boeck et al. . |
| 4,293,482 | 10/1981 | Abbott et al. . |
| 4,293,483 | 10/1981 | Debono . |
| 4,293,485 | 10/1981 | Debono . |
| 4,293,487 | 10/1981 | Debono . |
| 4,293,488 | 10/1981 | Debono . |
| 4,293,489 | 10/1981 | Debono . |
| 4,293,490 | 10/1981 | Abbott et al. . |
| 4,293,491 | 10/1981 | Debono . |
| 4,299,762 | 11/1981 | Abbott et al. . |
| 4,299,763 | 11/1981 | Abbott et al. . |
| 4,304,716 | 12/1981 | Abbott et al. . |
| 4,320,053 | 3/1982 | Abbott et al. . |
| 4,320,054 | 3/1982 | Abbott et al. . |
| 4,322,338 | 3/1982 | Abbott et al. . |
| 4,931,352 | 6/1990 | Fromtung et al. .......... 435/71.3 |
| 4,968,608 | 11/1990 | Giacobbe et al. .......... 435/254 |

FOREIGN PATENT DOCUMENTS

| | | |
|---|---|---|
| 859067 | 2/1977 | Belgium . |
| 57549 | 8/1977 | Belgium . |
| A10032009 | 7/1981 | European Pat. Off. . |
| A20311193 | 4/1989 | European Pat. Off. . |
| A30311194 | 4/1989 | European Pat. Off. . |
| 2803581 | 8/1979 | Fed. Rep. of Germany . |
| 2050385A | 1/1981 | United Kingdom . |

OTHER PUBLICATIONS

Benz, et al, Helv. Chim. Acta 57,8, 2459-77 (1974).
Traber et al, Helv. Chim. Acta 62,4, 1252-67 (1979).
Roy et al, J. Antibiotics, XL, 3, 275-80 (1987).
Mukhopadhyay et al, J. Antibiotics, XL, 3, 281-89 (1987).
Gordee et al, J. Antibiotics XXXVII, 9, 1054-65 (1984).
Debono, M. et al, J. Antibiotics 42, No. 3, 389 (1989).
Debono, M. et al, Annals N.Y. Acad. Sci., 152 (1988).
Pache, W. et al, 13th International Congress Chemotherapy (1983), PS4,8/3, Part 115, Abstract No. 10; also referenced in Ann. Reports in Med. Chem. 19, Sec. III, 130-131.
CRC Handbook of Antibiotic Compound, vol. IV, Part I, pp. 355-367.

Primary Examiner—Herbert J. Lilling
Attorney, Agent, or Firm—Alice O. Robertson; Hesna J. Pfeiffer

[57] ABSTRACT

An antibiotic agent produced by the cultivation of Zalerion arboricola which is a cyclic lipopeptide with very high activity against human pathogens and of very low mammalian toxicity and its production and isolation are described.

6 Claims, 1 Drawing Sheet

ANTIBIOTIC AGENT PRODUCED BY THE CULTIVATION OF ZALERION MICROORGANISM IN THE PRESENCE OF MANNITOL

The present invention is concerned with a compound produced by fermentation or cultivation of the microorganism *Zalerion arboricola* and particularly concerned with methods for enhanced production of the compound. The compound is useful as an antifungal agent and as an antipneumocystis agent. The compound, its use and methods of obtaining the compound are disclosed in copending applications Ser. No. 374,416, and Ser. No. 492,025 (Attorney Docket No. 17951-IA).

DESCRIPTION OF THE INVENTION

The present application is directed especially to improved processed for obtaining the compound. The compound which has been found to be useful as an antifungal agent and as an antipneumocystis agent is produced on cultivation of *Zalerion arboricola* under aerobic conditions and is represented by the formula

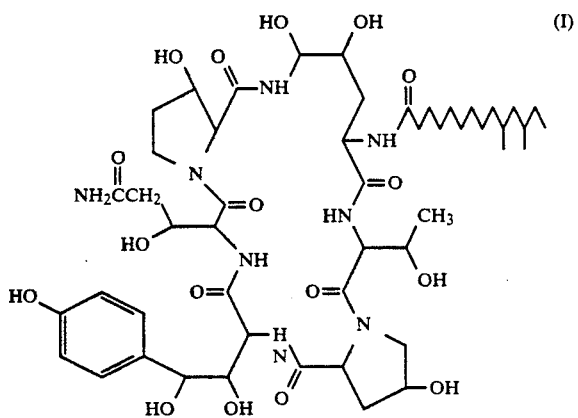

The compound may be named: 1-[4,5-dihydroxy-$N^2$-(10,12-dimethyl-1-oxotetradecyl)-ornithine]-5-(3-hydroxyglutamine)-6-(3-hydroxy proline)echinocandin B.

The preferred stereoisomer is thought to be: 1-[4,5-dihydroxy-$N^2$-(10,12-dimethyl-1-oxo-tetradecyl)-L-ornithine]-5-(3-hydroxy-L-glutamine)-6-[3-hydroxy-L-proline]echinocandin B.

The present invention embraces improved methods for producing compositions enriched in the compound of formula (I) or in improving the rate of production of the compound.

The structure of the compound has been determined by detailed analyses of the spectral characteristics.

MASS SPECTRAL DATA

Electron impact (EI) mass spectral data were obtained on a Finnigan-MAT 212 mass spectrometer at 90 eV. Gas Chromatograph-Mass Spectrogram (GC-MS) analyses of the TMS (trimethylsilyl) derivatives of total acid hydrolysates were performed in the same instrument. Fast atom bombardment (FAB) mass spectra were recorded on a VG20-253 instrument.

Compound IA has the molecular weight 1064 by FAB-MS (observed (M+Li)+ at m/z 1071). GC-MS of the total acid hydrolysate disclosed one equivalent each of threonine, 4-hydroxyproline, 3-hydroxyglutamic acid, 3-hydroxyproline, and a $C_{16}$ saturated fatty acid.

NMR SPECTRAL DATA

Compound I $^1$H NMR spectrum: in CD$_3$OD at 400 MHz is as seen in FIG. 1; and $^{13}$C NMR Chemical shifts obtained in CD$_3$OD at 75 MHz in ppm relative to TMS at zero ppm using solvent peak at 49.0 ppm as internal standard: 11.6, 19.7, 20.2, 20.7, 27.0, 28.1, 30.30, 30.34, 30.6, 30.8, 31.18, 31.24, 32.9, 34.5, 34.8, 36.7, 38.1, 38.5, 39.4, 45.9, 47.0, 51.4, 55.6, 56.3, 57.1, 58.3, 62.5, 68.2, 69.8, 70.55, 70.68, 71.3, 73.9, 74.3, 75.8, 76.9, 116 2(2X), 129.6(2X), 133.0, 158.5, 169.1, 172.5, 172.7, 172.9, 173.4, 174.5, 175.8, 177.2 ppm.

On the basis of these and other data, Compound I is believed with considerable certainty to have the structure indicated.

The compound is a white solid soluble in organic solvents such as methanol, ethanol, dimethylformamide, dimethyl sulfoxide, ethyl acetate and the like.

The compound of this invention has antifungal properties against both filamentous fungi and yeasts. It is particularly useful against organisms causing pathogenic mycotic infections such as *Candida albicans*, *Candida rugosa*, *Candida parapsilosis* and the like, where not only high activity is exhibited but consistently high activity over an expanded panel of strains of the organisms is exhibited.

Moreover, unlike a number of antifungal agents, such as amphotericin B, which while active against *Candida albicans* and certain other fungal pathogens, are limited in their utility because of the untoward and dangerous side effect, the agents of the present invention are not only a very effective antifungal agents but are substantially non-toxic and substantially free of undesirable side reactions.

Red blood cell lysis, a harmful and potentially fatal side reaction is shown by many compounds at concentrations approaching the therapeutic dose and this property has limited the applicability of these compounds as drugs. The compound of formula (I) is expected to require a concentration far above that for therapeutic use before red blood cell lysis would occur.

The compound is also effective antifungally against filamentous fungi including Aspergillus sepcies, Penicillium species, Fusarium species, Alternaria species, Neurospora species and the like.

Furthermore, the compound is also useful as an agent for the treatment of *Pneumocystis carinii*, the causative agent of a pneumonia of particular severity to immune-compromised patients such as those with acquired immune deficiency syndrome, (AIDS).

The compound of the present invention is conveniently produced by cultivating a cultural of *Zalerion arboricola*, identified as MF 5171 in the Merck cultural collection, which is deposited under the Budapest Treaty in the Culture Collection of the American Type Culture Collection at 12301 Parklawn Drive, Rockville, MD 20852 and is accessible under the accession number ATCC 20868.

The colonial and morphological description of ATCC 20868 are set forth below:

Colonies on potato-dextrose agar (Difco) at 20 C slow-growing, attaining a diameter of 8–12 mm in one week. Mature colonies (3–4 weeks) on potato-dextrose agar effuse, with submerged and aerial hyphae, surface hairy, lanose, or funiculose, dull to moderately shiny, forming raised, densely compact colonies, with a substromatic texture due to dense conidia formation. Colony color pale olive-brown, olive, olive-brown finally olive-black, Isabella Color, Sayal Brown, Tawny-olive, Saccardo's Umber, Sepia, Brownish Olive, Raw Umber, Dark Olive, Olivaceous Black (capitalized color names from R. Ridgway. 1912. Color Standards and Nomenclature, Washington, D.C.). Same colors in colony reverse. Odor, exudates, and soluble pigments absent.

Hyphae (in 3% KOH) pale yellow-brown to olive-brown, septate, branched, often with irregular lateral or terminal lobes, 1-3 μm wide, thin- to slightly thick-walled, with walls smooth to slightly incrusted or verrucose. Aerial hyphae often adhering together in fascicles. Setae and hyphopodia absent.

Conidiogenous cells monoblastic, scattered to denfe, integrated, terminal and intercalary, arising directly from undifferentiated hyphae, at right to slightly acute angles. Conidia originating as irregular chains, filaments, or coils, later developing as compact, irregular masses of 6-25 cells. Individual conidial cells, 3-6 μm in diameter, globose, subglobose, or slightly irregular to lobed, smooth to finely verruculose, yellow-brown to olive brown.

Although the production of the novel compounds are discussed hereinbelow principally with respect to a specific strain, ATCC 20868, all strains of the genus *Zalerion arboricola* and mutants are contemplated within the scope of this invention.

However, one particular mutant identified in the Merck Culture Collection as MF-5404 and accessible from the American Type Culture Collection as *Z. arboricola* ATCC 20957 is particularly useful in the production of Compound I. The use of this mutant in the production of Compound I, hereinafter described, is more fully described and claimed in co-pending application Ser. No. 492,024 Attorney Docekt No. 18022, the teachings of which are incorporated by reference.

Compound I may be produced by cultivating *Zalerion arboricola* in a suitable nutrient medium under conditions hereinafter described and thereafter recovering from the production by medium extracting the active component from the fermentation medium with a suitable solvent, concentrating the solution containing the desired component, and then subjecting the concentrated material to chromatographic separation to separate Compound I from other metabolites also present.

Compound X which is the subject of copending application Ser. No. 362,647, filed June 7, 1989 which is a continuation of Ser. No. 105,795, filed Oct. 10, 1987, now abandoned, and named therein as 1[(4R,5R) 4,5-dihydroxy-$N^2$-(10,12-dimethyl-1 oxotetradecyl)-L-ornithine]5-(threo-3-hydroxy-L-glutamine)echinocandin B also is produced by the organism.

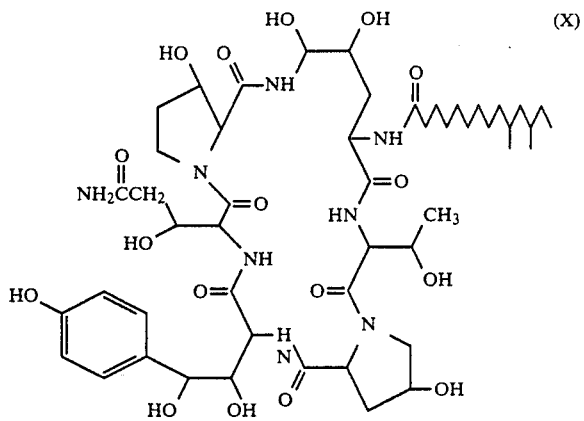

It is preferred therefore, in order to favor the production of Compound I, that the nutrient medium be modified or a method of directed synthesis be employed mutant be employed as hereinafter described.

PRODUCTION

The production of the compound of the present invention may be carried out by one of several methods. One method is directed biosynthesis, carried out by substituting in the fermentation medium, an amino acid analog not normally present in such medium as the primary source of nitrogen. Incorporation of unnatural amino acids hereinafter referred to as "analog incorporation" or "directed synthesis" has been found to increase the formation of Compound I in the fermentation medium and constitutes an aspect of the present invention. In such directed synthesis, the unnatural amino acid becomes the primary source of nitrogen. One of the most effective amino acids for directing the synthesis is 3,4-dehydroproline. Other useful amino acids include L-proline and L-azetidine-2-carboxylic acid.

When analog incorporation is employed, the medium may be an otherwise conventional medium. Thus, as nitrogen sources there may be in addition to the unnatural amino acids, complex sources which supply nitrogen such as yeast hydrolysates, yeast autolysates casein hydrolysates and the like. Generally, the sources of carbon include glycerol, sugars, starches and other carbohydrates, or carhohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 40 percent by weight of the medium is satisfactory. These carbon sources can be used individually or several such carbon sources may be combined in the same medium.

Among the nutrient inorganic salts, which can be incorporated in the culture media are the customary slats capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Typical useful media are the following:

| Medium I | |
|---|---|
| Glycerol | 85.0 g |
| Pectin | 10.0 g |

-continued

| | |
|---|---|
| Peanut Meal | 4.0 g |
| Peptonized Milk | 4.0 g |
| Tomato Paste | 4.0 g |
| Corn Steep Liquor | 4.0 g |
| Lard Water | 4.0 g |
| Glycine | 2.0 g |
| $KH_2PO_4$ | 2.0 g |
| Distilled Water | 1000.0 ml |
| Pre Sterile pH = 7.0 | |
| Medium II | |
| Cerelose | 20.0 g |
| Pharmamedia* | 2.5 g |
| 85% Lactate | 2.0 g |
| $KH_2PO_4$ | 15.0 g |
| Trace Elements | 10.0 ml |
| Distilled Water | 1000.0 ml |
| pH 7.0 | |

| Trace Elements | Per liter of 0.6N HCl |
|---|---|
| $FeSO_4.7H_2O$ | 1.0 g |
| $MnSO_4.4H_2O$ | 1.0 g |
| $CuCl_2.2H_2O$ | 0.025 g |
| $CaCl_2$ | 0.1 g |
| $H_3BO_3$ | 0.056 g |
| $(NH_4)_6Mo_7O_{24}.4H_2O$ | 0.019 g |
| $ZnSO_4 7H_2O$ | 0.2 g |

*Pharmamedia is a commercial nutrient media, the principal component which is nonhydrolyzed globular protein derived from cottonseed and available from Traders Protein, Buckeye Cellulose Corporation, Memphis, Tenn. 38108.

Compound I may be produced by the "analog incorporation" method in a manner somewhat as follows: a frozen vial of Zalerion arboricola culture ATCC 20868 is inoculated into an appropriate seed medium of pH in the range 5 to 8.1, optimally 6 to 7.5, and grown for from 2 to 30 days, preferably 2 to 5 days, at temperatures in the range of 15° C. to 30° C., preferably 25° C.-26° C. with or without agitation. Agitation, when employed, may be up to 400 rpm. preferably about 200 to 220 When the growth becomes abundant, the culture is used to inoculate the medium to be modified by analog incorporation and to be cultivated for production of the secondary metabolite.

The analog is added five days after growth has been established in an amount to provide a final concentration of 5-8 mg/ml.

The fermentation is conducted for a minimum of 14 days at 25° C.-26° C. with agitation at 220 rpm.

At the end of this period, the whole broth is extracted with an equal volume of a solvent such as methyl ethyl ketone. Other suitable solvents include ethyl acetate and acetone. The solvent is then removed under reduced pressure to obtain a residue which may be solubilized with a known volume of methanol, dried and assayed by HPLC, and the remaining material subjected to isolation procedures.

When directed synthesis is not employed as a method for production, conventional materials may be employed.

Thus as sources of nitrogen there may be employed ammonium salts, amino acids such as glycine, arginine, threonine, methionine and the like as well as complex nutrients such as yeast hydrolysates, yeast autolysates, yeast cells, tomato paste, soybean meal, casein hydrolysates, yeast extracts, corn steep liquors, distillers solubles, cottonseed meal, meat extract, and the like. The various sources of nitrogen can be used alone or in combination in amounts ranging from 0.2 to 10 percent by weight of the medium.

As sources of carbon, materials previously detailed may be employed, although compositions containing glycerol or mannitol are preferred. Medium I, previously described, illustrates a glycerol containing medium. The following media, designated RG2 and RG120 are illustrative of mannitol containing media:

| RG2 MEDIUM | per liter | RG120 MEDIUM | per liter |
|---|---|---|---|
| Mannitol | 44 g | Mannitol | 91 g |
| Corn Steep Liquor | 4 g | Corn Steep Liquor | 4 g |
| Lard Water | 4 g | Lard Water | 4 g |
| Pectin | 10 g | Pectin | 10 g |
| $KH_2PO_4$ | 2 g | $KH_2PO_4$ | 2 g |
| Tomato Paste | 4 g | Tomato Paste | 4 g |
| Peptonized Milk | 4 g | Peptonized Milk | 4 g |
| Glycine | 2 g | Glycine | 2 g |
| Peanut Meal | 4 g | Peanut Meal | 4 g |
| pH adjusted to 7.0 | | pH adjusted to 7.0 | |

Moreover, it has been discovered that by use of certain mannitol containing media, the production of the desired product may be enhanced. The improved production may be manifest in the increased yield of Compound I with respect to Compound X or in the more rapid formation of all the metabolites.

The rate of production may be increased several-fold by the use of mannitol in an amount of at least 4 percent by weight in a medium with careful pH control at about 5.5 in which the nitrogen source is hydrolyzed casein and yeast nitrogen base. For maintaining critical pH cotorl, the presence of a phosphorus containing buffer, preferably monobasic potassium phosphate is important. Representative of suitable liquid media are those designated TG102 and TG103.

| TG102 MEDIUM | per liter | TG103 MEDIUM | per liter |
|---|---|---|---|
| D-Mannitol | 40 g | D-Mannitol | 40 g |
| Bacto-Peptone | 33 g | NZ-Amine (type E)* | 33 g |
| Bacto-Yeast Extract | 10 g | Fidco-Yeast Extract | 10 g |
| $(NH_4)_2SO_4$ | 5 g | $(NH_4)_2SO_4$ | 5 g |
| $KH_2PO_4$ | 9 g | $KH_2PO_4$ | 9 g |
| no pH adjustment | | no pH adjustment | |

*Casein hydrolysate, Humko-Sheffield, Memphis, Tenn.

Certain mannitol containing media moreover, favor the production of Compound I of the present invention relative to Compound X which is normally the major product on the cultivation of Zalerion arboricola. By use of these media, the yield of Compound I has been found to be significantly increased. Thus, a medium which is substantially neutral and which contains D mannitol as carbon source, a milk protein hydrolysate (peptonized milk) as a complex nitrogen source, glycine as amino acid and buffer, a phosphorus containing buffer and preferably also containing lactic acid, trace elements, and selected vegetable oils. Suitable oils are soy, peanut and sunflower oils. The useful ranges are as follows:

| | grams/liter |
|---|---|
| D-mannitol | 20–100 |
| $KH_2PO_4$ | 0.5–3 |
| glycine | 1–4 |
| Peptonized milk | 2–20 |
| Lactic acid | 0–3 |
| Trace elements (previously detailed) | 0–15 ml |
| Vegetable oil (soy, peanut or sunflower) | 0–20 |

-continued

| | grams/liter |
|---|---|
| presterilization pH = 7 | |

For best yield of the compound, all of the components of the foregoing composition should be present. Thus, S6 medium (below) is a preferred medium.

| S2 MEDIUM | | S6 MEDIUM | |
|---|---|---|---|
| D-Mannitol | 44 g | D-Mannitol | 44 g |
| KH$_2$PO$_4$ | 2 g | KH$_2$PO$_4$ | 2 g |
| Glycine | 2 g | Glycine | 2 g |
| Peptonized milk | 15 g | Peptonized milk | 15 g |
| Lactic acid | 2 g | Lactic acid | 2 g |
| Trace elements (previously detailed) | 10 ml | Trace elements (previously detailed) | 10 ml |
| | | Soybean oil | 10 g |
| pre-sterilization pH 7.0 | | pre-sterilization pH 7.0 | |

In addition to liquid media, solid media may be employed. The following are representative:

| | per 250 ml flask | Base liquid | per liter |
|---|---|---|---|
| F204 SOLID MEDIUM | | | |
| Millet | 15 g | Ardamine PH** | 33.0 g |
| Base liquid | 15 ml | Sodium Tartrate | 6.6 g |
| | | FeSO$_4$.7H$_2$O | 0.66 g |
| | | Monosodium Glutamate | 6.6 g |
| | | Corn Oil | 6.6 ml |
| | | no pH adjustment | |
| F4-SF SOLID MEDIUM | | | |
| Cracked corn | 15 g | Ardamine PH | 0.2 g |
| Base liquid | 10 ml | KH$_2$PO$_4$ | 0.1 g |
| | | MgSO$_4$7H$_2$O | 0.1 g |
| | | Sodium Tartrate | 0.1 g |
| | | FeSO$_4$.7H$_2$O | 0.01 g |
| | | ZnSO$_4$.7H$_2$O | 0.01 g |
| | | no pH adjustment | |

**(yeast autolysate available from Yeast Products Inc., Clifton, New Jersey)

The foregoing media may be employed in fermentations carried out using a standard procedure wherein first, a frozen vegetative mycelia of *Zalerion arboricola* (ATCC 20868) are thawed and used to inoculate a seed medium which is then incubated for a minimum of 3 days to produce organisms which serve as seeds in the production of Compound I. The seed medium may be of the following composition.

| Seed Medium (KF Medium) | |
|---|---|
| Corn steep liquor | 5.0 g |
| Tomato paste | 40.0 g |
| Oat flour | 10.0 g |
| Glucose | 10.0 g |
| Trace elements* | 10.0 ml |
| Water | 1000 ml |
| pH = 6.8 | |

*previously detailed

In this process, a slant section of a preserved culture of ATCC 20868 is inoculated into a liquid nutrient seed medium of pH in the range 5 to 8.1, optimally 6 to 7.5, and the flasks incubated with agitation at temperatures in the range of from about 15° C. to abut 30° C., preferably 20° C. to 28° C. Agitation, may be up to 400 rpm, preferably, about 200 to 220 rpm. The incubation is carried out over a period of from 2 to 30 days, preferably 2 to 14 days. When growth is abundant, usually between 2 and 5 days, the growth may be used to inoculate the production medium for the production of Compound I. Preferably however, a second stage fermentation is carried out, inoculating with a portion of the culture growth and then employing similar conditions but generally with a shortened incubation period of about 1 to 3 days. The growth then is employed to inoculate the production medium.

The fermentation production medium inoculated with the culture growth is incubated for 3 to 30 days, usually 7 to 14 days, with or without agitation. The fermentation may be conducted aerobically at temperatures ranging from about 20° C. to about 40° C. For optimum results, it is most convenient to conduct these fermentations at a temperature in the range of from about 24° C. to about 30° C. Temperatures of about 24° C.–28° C. are most preferred. The pH of the nutrient medium suitable for producing the instant compounds can vary from about 5.0 to 8.5 with a preferred range of from about 6.0 to 7.5. However, for rapid production, the pH should be closely maintained at about 5.5. After the appropriate period for the production of the desired compound or compounds, the latter is recovered from the fermentation medium as hereinafter more fully described.

In addition to the foregoing, an improved method for producing Compound I utilizes a specific mutant of *Zalerion aboricola* in the fermentation. This specific mutant was first obtained by subjecting *Z. arboricola* 20868 to a mutagenic agent and isolating the colonies produced. A single colony from about eighty colonies was found to be useful in producing Compound I as the major component. The mutant, its preparation and properties is the subject of copending application Ser. No. 492,024 Attorney Docket No. 18022, the teachings of which are incorporated by reference. The mutant, retained in the Merck culture collection as MF5404 has been deposited in the permanent culture collection of the American Type Culture Collection and is available under the accession number ATCC 20957. The mutant may be employed in substantially the same way as with the parent microorganism as is subsequently briefly described and more fully described in the copending application. Thus fermentation employing this mutant may be carried out employing the above conditions of temperature and pH in the nutrient media above disclosed, preferably in one of the media identified as S6, TG102 or TG103 for a suitable period of up to about 30 days. After completion of the cultivation, the products are harvested and Compound I isolated.

HARVESTING AND ISOLATION

After production by cultivation employing one of the above-described methods, Compound I is harvested and isolated from the medium.

The exact steps may vary somewhat depending on whether the fermentation is carried out in liquid or solid medium, what solvent is employed and what adsorbent or combination of adsorbents is employed.

When the fermentation is carried out on a solid medium, the first step may be carried out by adding an alcoholic solvent to the fermentation medium, thoroughly mixing, then filtering, recovering and concentrating the aqueous alcohol filtrate The concentrated filtrate may be first back-extracted or washed with a lower aliphatic hydrocarbon solvent such as hexane or other alkane to remove alkane soluble impurities. The alkane washed filtrate may be extracted or partitioned with a water-immiscible oxygenated organic solvent and the resulting solution concentrated, then placed onto a chromatographic column for at least one, generally several separation steps. Suitable columns are silica gel, reverse phase silica gel and "Sephadex" LH-20 (Pharmacia) dextran absorbent.

When the fermentation is carried out in a liquid medium, in one method, the mycelial solids are filtered and recovered from the fermentation medium. Alcohol is added to the mycelial cake, and the mycelial solid thoroughly mixed with the alcohol, filtered, and the filtrate collected and concentrated. In an alternative method, the whole broth can be extracted by the addition of one volume of alkanol, preferably methanol, and filtered to remove solid impurities. The alkanol extract is then adsorbed on "Diaion" HP-20 (styrene-divinylbenzene copolymer, Mitsubishi Chemical Industries, Ltd) resin and eluted with 100% alkanol. "Diaion" SP 207 (brominated) or other commercially available styrene-divinyl-benzene copolymer also may be employed. A second dilution/HP-20 adsorption/elution step is utilized to concentrate the sample in preparation for chromatographic separations. Sometimes, a third dilution/HP-20 adsorption/elution step may be desirable for volume reduction.

The alcoholic solvent to be employed in the initial extraction of the active agent from the solid nutrient medium or from the mycelial pad may be any of the lower alcohols such as methanol, ethanol, isopropanol, and the like. Methanol is preferred.

If the active agent is partitioned from the alkanol or methanol solution, then suitable solvents are esters, such as ethyl acetate, isopropyl acetate, butyl acetate, or ketones, such as methyl ethyl ketone.

The chromatographic separation may be carried out by employing conventional column chromatography with non-ionic resin or by high performance liquid chromatography employing reverse phase resin. The fractions containing the antibiotic Compound I may be detected by antifungal assay using *Candida albicans*. Generally, more than one chromatographic separation steps are employed. In a most preferred procedure, one or more separations are carried out employing column chromatography and a final separation is carried out employing high performance liquid chromatography (HPLC) with $C_{18}$ reverse phase resin.

When conventional column chromatography is employed for chromatographic separations, silica gel is the preferred adsorbent. Usually more than one chromatographic separation is employed. Silica gel may be used in all the separations while employing different eluting agents. However, it may be combined advantageously with the use of a different adsorbent such as a dextran adsorbent sold under the trade name of "Sephadex" LH-20. Other adsorbents such as alumina, styrene-divinylbenzene copolymers available commercially as "Diaion" HP-20, HP 30, HP-40, SP-207 and "Amberlite" XAD-2, XAD-4, XAD-16 (Rohm and Haas Co.) also may be employed.

In the fractionation and recovery of the active component by chromatography on silica gel, ester/alcohol mixtures with increasing concentration of alcohol provide good separations. A mixture of ethyl acetate and methanol has been found to be especially useful. These may be employed in isocratic, step gradient or continuous gradient systems. When a dextran adsorbent such as "Sephadex" LH-20, is employed, a chlorohydrocarbon/hydrocarbon/ alcohol solvent system may be employed. A mixture of methylene chloride/hexane/methanol has been found to be especially useful.

In carrying out the HPLC separation, the alcohol solution containing material recovered from the conventional chromatography is concentrated and the residue dissolved in methanol/water in the same ratio as found in the mobile phase and placed on a column packed with commercial reverse phase resin or on a column filled with silica gel/$C_{18}$ reverse phase resin prepared as amply reported in the literature. Alternatively, the alcohol solution may be diluted to 52 percent with water and pumped onto the column. The column is operated using methanol/water (1:1 or optionally other ratios) at 800–2000 psi which produces a flow rate of about 20 ml/min. Separation is monitored at 210 nm.

The fractions are assayed for activity with *Candida albicans* and analytical HPLC. The product is recovered from any of the chromatographic procedures by combining the *Candida albicans* active fractions and concentrating under reduced pressure.

The superior properties of Compound I as a therapeutic agent in the treatment of mycotic infections may be illustrated with minimum fungicidal concentration (MFC) results in tests against *Candida albicans*, *Candida tropicalis* and *Candida parapsilosis*.

The activity may be seen in a microbroth dilution assay employing as medium a Yeast Nitrogen Base (Difco) with 1% dextrose (YNBD). In carrying out the assay, Compound I was solubilized in 10 percent dimethyl sulfoxide (DMSO) and diluted to 2560 $\mu$g/ml. The compounds were further diluted to 256 $\mu$g/ml in YNBD. Then 0.15 ml of the suspension was dispensed to the first row of a 96-well plate (each well containing 0.15 ml of YNDB) resulting in a drug concentration of 128 $\mu$g/ml. Two-fold dilutions were then made to obtain final drug concentrations ranging from 128 to 0.06 $\mu$g/ml.

The yeast cultures, maintained on Sabouraud dextrose agar were transferred to YM broth (Difco) and incubated overnight at 35° C. with shaking (250 rpm). After incubation, each culture was diluted in sterile water to yield a final concentration of 1–5 x $10^6$ colony forming units (CFU)/ml.

96-well microplates were inoculated using a MIC-2000 (Dynotech) which delivers 1.5 $\mu$l per well yielding a final inoculum per well of 1.5–7.5 $\times 10^3$ cells. The microplates were incubated at 35° C. for 24 hours. The minimum inhibitory concentrations (MICs) were recorded as the lowest concentrations of drug showing no visible growth.

After recording the MIC, the plates were shaken to resuspend the cells. Thereafter, 1.5 $\mu$l samples from the wells in the 96-well microplate were transferred to a single well tray containing Sabouraud dextrose agar. The inoculated trays were incubated 24 hours at 28° C. and then read. The MFC is defined as the lowest concentration of drug showing no growth or less than 4 colonies per spot.

| Fungus Strain No. | Minimum Fungicidal Concentration ($\mu$g/ml) Compound I |
|---|---|
| *Candida albicans* | |
| MY 1585 | 0.5 |
| MY 1208 | 0.5 |
| MY 1028 | 1.0 |
| MY 1750 | 0.25 |

| Fungus Strain No. | Minimum Fungicidal Concentration (µg/ml) Compound I |
|---|---|
| MY 1783 *Candida tropicalis* | 0.5 |
| MY 1012 *Candida parapsilosis* | 2.0 |
| MY 1009 | 8.0 |
| MY 1010 | 8.0 |

The foregoing results are exemplary of the superior and consistent antimycotic properties showing by Compound I.

The compound has potential as a replacement for a known antifungal agent which while effective as an antifungal agent is of limited utility for having lytic effect on red blood cells at low dose levels.

The compound is also a broad spectrum antifungal agent effective against many fungal species, both filamentous fungi and yeasts.

The compound is useful for inhibiting or alleviating *Pneumocystis carinii* infections. In such use, Compound I is administered in an therapeutically effective or inhibitory amount to subjects infected with or to immune compromised subjects susceptible to being infected with *Pneumocystis carinii*. The efficacy of Compound I for therapeutic or anti-infective purposes may be demonstrated in studies on immunosuppressed mice or rats.

In a representative study ten male C3H/HeJ mice, weighing 22-24 gms. each, were immunosuppressed by the addition of dexamethasone to the drinking water (8.0 mg/L) for six weeks to induce the development of *P. carinii* infections. To enhance the infection the mice were also maintained on a low protein diet. At the beginning of the seventh week the mice were divided into two groups. Both groups continued to receive dexamethasone in the drinking water and low protein diet for the remainder of the study. Mice in Group I were injected intraperitoneally twice daily with 0.5 ml of a 20% DMSO solution as a vehicle control. Mice in Group II were injected intraperitoneally twice daily with 0.5 ml of sterile water containing 0.0125 mg of Compound I (dissolved in DMSO, final concentration of DMSO is 10%, actual dose, 0.5 mg/µg). The treatment period lasted two weeks.

At the end of the treatment period (a total of eight weeks immunosuppression) the animals were sacrificed and the lung tissues removed. The tissue was then processed to determine the number of cysts for each animal. Compound I reduced the number of cysts by 81% as compared to the control animals.

The outstanding properties are most effectively utilized when the compound is formulated into novel pharmaceutical compositions with a pharmaceutically acceptable carrier according to conventional pharmaceutical compounding techniques.

The novel compositions contain at least a therapeutic antifungal or antipneumocystis amount by weight of the active compound. Generally, the compositions contain at least 1 percent by weight of Compound I. Concentrate compositions suitable for dilutions prior to use may contain 15 percent or more and with some compositions 90 percent or more by weight. In preparing the compositions, Compound I is intimately admixed with any of the usual pharmaceutical media.

The compositions may be prepared in forms for oral, parenteral, topical or pulmonary (inhalation) administration. Oral administration may be with liquid or solid preparations. For liquid preparations, the therapeutic agent is formulated with liquid carriers such as water, glycols, oils, alcohols, and the like. For solid preparations such as capsules and tablets, the therapuetic agent is formulated with solid carriers such as starches, sugars, kaolin, ethyl cellulose, calcium and sodium carbonate, calcium phosphate, kaolin, talc, lactose, generally with lubricant such as calcium stearate, together with binders, disintegrating agents and the like. Because of their ease in administration, tablets and capsules represent the most advantageous oral dosage form.

Compound I may be formulated in therapeutic compositions for infection. Further, it may be presented in unit dosage form, in ampoules or in multidose containers, and if necessary with an added preservative. The injectable compositions may take such forms as suspensions, solutions or emulsions in oily or aqueous vehicles such as 0.85 percent sodium chloride or 5 percent dextrose in water, or may be solubilized in alcohol/propylene glycol or polythelene glycol and may contain formulating agents such as suspending, stabilizing and/or dispersing agents. Buffering agents as well as other additives may be added. Alternatively, the active ingredients may be in powder form for reconstituting with a suitable vehicle prior to administration.

The compositions may be formulated in unit dosage form. The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention may contain, depending on use, from 35 to 200 milligrams or more of the component drug.

If the application is to be topical, the drug may be formulated in conventional creams and ointments such as white petrolatum, anhydrous lanolin, cetyl alcohol, cold cream, glyceryl monostearate, rose water and the like. Usually a 1 to 2 percent cream solution is prepared and applied to the area to be treated.

For antipneumocystis use, administration by inhalation may be particularly useful. For administration by inhalation, Compound I may be delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of Compound I in suitable propellants, such as fluorocarbons or hydrocarbons.

Because of the difficult solubility of the compound in pharmaceutically acceptable liquid carriers and because of desirability to directly treat lung and bronchi, aerosol administration is a preferred method of administration Insufflation is also a desirable method, especially where infection may have spread to ears and other body cavities.

For non-medical application, the product of the present invention, may be employed in compositions in an inert-carrier which includes finely divided dry or liquid diluents, extenders, fillers, conditioners and excipients, including various clays, diatomaceous earth, talc, and the like, or water and various organic liquids such as lower alkanols, for example ethanol and isopropanol, or kerosene, benzene, toluene and other petroleum distillate fractions or mixtures thereof.

In practicing the invention, an antifungal amount of the compositions may be applied directly to areas where fungal control is desired.

The following examples illustrate the invention but are not to be construed as limiting:

EXAMPLE I

A frozen culture of MF-5171 *Zalerion arboricola*, ATCC No. 20868, maintained in the Merck culture collection was employed in the fermentation.

The entire slant of a 2.5 ml frozen culture was defrosted and aseptically transferred to a 250 milliliter 3-baffle flask containing 40 milliliters of Medium I (composition previously detailed).

Medium I, inoculated with culture, was incubated at 26° C. for five days with agitation at 220 rpm to obtain mature seed broth.

Seed broths were similarly prepared from Medium II of the composition also previously detailed. Seeds from Medium I and Medium II were then inoculated in 7.5 milliliters of Medium I and Medium II, respectively, at a level of 5 percent and incubated at 26° C. to establish growth. At the end of this period, the following amino acids were added to the separate tubes of each medium: L-proline. D-proline. L-azetidine-2-carboxylic acid, and 3,4-dihydro-L-proline, and Compound X as control. The tubes were incubated at 26° C. at 220 rpm for 14 days.

At the end of this period the broth in each of the tubes was diluted with an equal volume of methanol, the mixture homogenized and clarified by filtration. The methanol mixture was subjected to reduced pressure to remove the methanol and recover a residue which then was extracted twice with 10 milliliters of ethyl acetate. The ethyl acetate solution was dried over magnesium sulfate.

In separate operations, the dried solutions were concentrated to dryness and reconstituted with 0.5 ml of methanol. Each resulting solution was diluted 1:5, and 10 µl of the diluted solution employed in an analytical HPLC assay on "Zorbax" ODS (DuPont) column using 1:1 acetonitrile/water with Compound X which had retention times of 8.38 minutes (Medium I) and 8.Z9 minutes (Medium II) as controls. The tube of Medium I to which L-proline and 3,4-dehydro-L-proline had been added and the tube of Medium II to which L-proline, L-azetidinecarboxylic acid and 3,4-dehydro-L-proline had been added showed retention peaks in the range 7.39–7.48 minutes in addition to a retention time of 8.28–8.38 minutes attributable to Compound X.

HPLC bioautographic assays were also carried out on the same 10 µl fermentation samples which had been used for analytical HPLC. 10 microliters of sample were used per injection and eluted with acetonitrile/water (1:1) at a flow rate of 1 ml/min and 200 microliter/cut with a void volume of 1.5 milliliters. The fractions were collected in a 96 well, microtiter plate. The HPLC solvent was evaporated and to each well was added 0.2 milliliter of potato dextrose broth which had been inoculated with *Candida albicans* MY-1028 and brown for 24 hours. Activity besides that attributable to Compound X was found in the sample obtained from the medium to which 3,4-dehydro-L-prOline had been added in the fraction, which corresponds to a peak found at 7.57 minutes. This peak corresponds to the 7.39 to 7.48 minutes found in the analytical HPLC evaluation.

A small amount of the compound was isolated from the HPLC bioautography determination. The FAB mass spectrum of this minor constituent from the directed biosynthesis using 3,4-dehydro-L-proline showed a molecular ion of 14 mass units lower than Compound X.

EXAMPLE II

Fermentation

The contents of one frozen vial (approximately 2 milliliters) of culture MF 5171 (*Zalerion arboricola*) were inoculated into 54 milliliters of KF seed medium in an unbaffled 250 milliliters Erlenmeyer flask. The culture was incubated at 25° C. for 3 days at 220 rpm on a reciprocal shaker. A sample of culture (5 ml) was inoculated into a 2-liter unbaffled Erlenmeyer flask containing 500 milliliters of the KF seed medium and cultivated at 25° C. for three days while shaking at 220 rpm.

At the end of the three day period, 5 milliliters of the culture was inoculated into each of five 2-liter unbaffled Erlenmeyer flasks containing 500 milliliters of the seed medium and cultivated at 25° C. for 3 days at 220 rpm. These flasks were pooled and inoculated into a 75-liter stirred vessel containing 50 liters of the production medium of the following composition:

| Production Medium | |
|---|---|
| Material | Concentration (g/L) |
| Corn Steep liquor | 5.0 mL |
| (NH$_4$)$_2$SO$_4$ | 2.0 |
| Lard water | 5.0 |
| CoCl$_2$6H$_2$O | 10.0 mg |
| Cod liver oil | 2.0 mL |
| Tomato paste | 5.0 |
| Na citrate | 2.0 |
| Glycerol | 75.0 |
| Polyethylene glycol 2000 | 2.0 mL | pH = 7.0 prior to sterilization at 121° C. for 35 minutes.

Cultivation was continued for 8 days at 25° C. at an agitation rate of 300 rpm and 5 liters/minute air flow. Thereafter, the fermentation broth was harvested for isolation.

Isolation

The whole broth of the foregoing 70 liter fermentation batch was filtered and the mycelial cake extracted with 10 liters of methanol. The methanol extract was filtered and diluted with 10 liters of water and adsorbed onto 1.2 liters of HP-20 resin and eluted with 100% methanol. The methanol rich cut, amounting to 1500 milliliters, was concentrated to 150 milliliters.

The concentrate was diluted to a 40% methanol/60% water mixture and adsorbed on 200 milliliters of HP-20. The column was washed successively with methanol, water (50:50), water, and acetonitrile/water (25:50), and then the metabolites eluted from the column with acetonitrile/water (50:50).

Seventy milliliters of the 400 milliliters of the cut from HP-20 adsorption, rich in biological activity, was diluted to 300 milliliters with water, filtered and charged at a flow rate of 10 ml/min onto an 88 milliliter "Zorbax" ODS column that had been equilibrated with acetonitrile/water (12.5/87.5). The column was eluted at a flow rate of 20 milliliters/minute with acetonitrile/water (40/60), followed by acetonitrile/water (50/50). The compounds were eluted with the 50/50 acetonitrile/water. The column was monitored via UV at 210 nm and antifungal assays with *Candida albicans* MY-1028, and analytical HPLC evaluations were made in the fractions. On the basis of these analyses, certain fractions were combined.

A sample of the combined fractions after concentration to dryness and evaluation by analytical HPLC was found to be a 1:1 mixture of Compound X and Compound I.

The foregoing sample which amounted to about 7.5 mg of Compound X and 7.5 mg of Compound I in 3.2 milliliters of methanol was diluted to 10 milliliters with water and injected on a "Dynamax" 60 A8μM C18 21.4 mn ID ×25 cm column (fitted with a 5 cm guard column (Rainin Instrument Co., Inc. Woburn, MA)) which previously had been equilibrated with acetonitrile/water (60/40). The mixture was then eluted with the same acetonitrile/water eluant at 10 milliliters/minute at ambient temperature and fractions of 15 milliliters each were collected. Thirty minutes after injection, a linear gradient over 60 minutes was initiated which increased the acetonitrile concentration from 40 percent to 60 percent. Readings at 210 nm and subsequent HPLC analysis of the cuts indicated that there were three fractions containing Compound I. The middle fraction containing the most and the purest Compound I was concentrated to dryness and a preliminary mass spectral determination made.

Lithiated fast atom bombardment mass spectra (FAB-MS) indicated the molecular weight to be 1064. Gas chromatogram mass spectra (GC-MS) of the trimethylsilyl(TMS) derivative of the total acid hydrolysate disclosed as maJor components threonine, 4-hydroxyproline, an oxidation product of ornithine like compound, 3-hydroxyglutamic acid, a $C_{16}$ fatty acid and 3-hydroxyproline. On the basis of this analysis, the structure of Compound I was proposed.

The component of this fraction was further purified by dissolving the fraction in 33 μl methanol, 100 μl water and 10 μl trifluoroacetic acid (TFA) and chromatographing the resultant solution on a Dynamax-60 A C18 10 mm ID 25 cm column which had been equilibrated with 55% 0.1% TFA in water/45% acetonitrile. Elution with the same solvent system at 4 ml/min at ambient temperature produced three fractions to have 210 nm adsorption peak. Two of the fractions were evaporated to dryness and analyzed for $^1$H NMR preliminary $^1$H NMR supported the formula of Compound I.

A purified sample of Compound I has the $^1$H NMR of FIG. 1 and the $^{13}$C NMR and mass spectral data previously detailed.

EXAMPLE III

Fifty milliliters of KF seed medium in a 250 milliliter unbaffled Erlenmeyer flask was inoculated with frozen vial of *Z. arboricola* and shaken at 220 rpm and 25° C. for 72 hour$. Two milliliters of this seed was used to inoculate 50 milliliters of KF medium and was grown for 72 hours. The second stage was used to inoculate the production medium.

Forty milliliters of medium previously detailed as Medium S-6 in 250 milliliter unbaffled Erlenmeyer flasks was inoculated with 2 milliliters of seed and the flasks shaken at 220 rpm and 25° C. for 14 days. A total of 125 flasks were pooled to obtain 5 liters of final broth.

The whole broth was vacuum filtered through a 1 inch bed of "Super-Cel" (Manville). No activity was detected in the filtered broth. The mycelium cake was extracted with 1 liter of methanol overnight with agitation. The methanol extract was assayed for presence of bioactive components using a disk diffusion assay with *C. albicans* MY1028 and HPLC assay (50/50 acetontrile/0.01 M potassium phosphate pH 7.0) and comparing results with previously obtained sample of Compound X as standard. The methanol extract was diluted to a final concentration of 50 percent aqueous methanol and adsorbed onto a 200 milliliter HP-20 column at a flow rate of 20 ml/min. The column was washed with three column volumes of 50 percent aqueous methanol. The activity was eluted with six column volumes of 75 percent aqueous methanol. The desired components were the appropriate fractions with Compound I and Compound X were combined to 1.7 liters.

The sample containing bioactive components was diluted with 1.7 liters of water to make the composition 50:50 methanol/water and the composition filtered to, remove insoluble particles. This preparation was then adsorbed onto an 88 milliliter "Zorbax" 0.05 column (Pre-equilibrated with 50:50 methanol/water) at 20 ml/min. The column was eluted with 45:55 acetonitrile/water at 20 ml/min; twenty milliliter fractions were taken after a 30 milliliter void volume. The chromatography was monitored via UV at 210 nm, via analytical HPLC and via antifungal bioassay (*C. albicans* MY1028). Certain fractions were combined, based mainly on analytical HPLC; a mixture of Compound I and Compound X which amounted to 80 milligrams was shown to contain 19.8 milligrams of Compound I.

EXAMPLE IV

The contents of a vial of frozen vegetative mycelia of *Zalerion arboricola*, ATCC 20868. was thawed and used to inoculate 54 milliliters of KF seed medium which was then incubated for 3 days at 25° C. at 220 rpm on a rotary shaker with a throw of 5 centimeters to produce a seed culture.

Two milliliters portions of the seed culture were inoculated into a 250-milliliter Erlenmeyer flask containing 50 milliliters of TG103 medium and incubated for 5 days at 25° C. with shaking.

At the end of this periOd, the fermentation broth was harvested. At harvest, the liquid culture was centrifuged to separate the cells from the culture supernatant. The cells were mixed with a 20-ml portion of methanol and the extraction was allowed to proceed overnight at room temperature. The solids were removed by centrifugation, and the methanolic extract was then inJected onto a 5 μ "Ultrasphere" (Beckman Engineering) column (4.6 mm ×25 cm) which was eluted isocratically with acetonitrile/water 48/52 at a flow rate of 0.75 ml/min. The effluent was monitored at 210 nm, and 0.25 ml fractions were collected in 96-well microtiter dishes. The solvent was removed from the dishes in vacuo, and the dishes were assayed for bioactivity by placing into each well a yeast extract, peptone, dextrose (YEPD) broth and of following composition:

|  | g/liter |
|---|---|
| Bacto yeast extract | 10 |
| Bacto peptone | 20 |

| | g/liter |
|---|---|
| Dextrose | 20 |
| no pH adjustment | | which had been seeded with *Candida albicans* MY1028 and incubating overnight at 37° C. The results showed the production of Compound I. Compound X is also produced.

EXAMPLE V 250 milliliter flasks were prepared containing 54 milliliters of KF seed medium (previously given) and inoculated from an agar slant of MF5404 *Z. arboricola* ATCC 20957 and incubated at 25° C. for four days at 220 rpm. A 20 milliliter sample was used to inoculate each of four 2 liter flasks containing 500 ml of KF medium. The flasks were incubated at 25° C. for three days at 220 rpm. The flask contents were then pooled for use as inoculum for a 300 liter seed fermenter containing 180 liters of KF medium and 2 ml/liter polypropylene glycol P-2000 (Dow Chemical Co.) added to reduce foaming. The seed fermenter was operated for three days at a temperature of 25° C, an air flow of 90 liters/min, a pressure of 0.7 kg/cm$^2$ gauge, and an agitator speed of 200 rpm. A 25 liter sample was used to inoculate an 800 liter production fermenter containing 475 liters of TG103 Medium of the composition previously given but to which 2 ml/liter of polypropylene glycol P-2000 had been added and sterilized at 120° C. for 25 minutes. The fermentation was carried out for five days at a temperature of 25° C., an air flow of 250 liters/minute, a pressure of 0.7 kg/cm$^2$ gauge, and an agitator speed of 150 rpm. The pH was allowed to decrease from an initial value of 6.0 to 5.5. and then maintained at 5.5±0.4 using NaOH and H$_2$SO$_4$. After five days the broth from two batches was harvested for product isolation.

Seven hundred and fifty liters of methanol was added to 750 liters of fermentation whole broth and the mixture agitated for 8 hours. The whole broth extract was centrifuged to remove the insoluble fermentation solids and to yield 1436 liters of clarified supernatant, which was adjusted to pH 7.

A 77 liter "Diaion" SP-207 (Mitsubishi Chemical Industries) bed was prepared by washing with methanol and pre-equilibrating with 50:50 methanol/water (MeOH/H$_2$O). The clarified supernatant was then charged to the SP-207 in an upflow direction at a fluidized bed rate of 5.7 liters per minute. After charging, the column was washed with 567 liters of 65:35 methanol water and eluted with 454 liters 100% methanol.

The MeOH/H$_2$O 65:35 and 100% MeOH SP-207 cuts from the SP-207 column were combined and adjusted to a composition 50:50 of MeOH/H$_2$O by the addition of H$_2$O to yield a 945 liter rich cut. This rich cut was charged to a 108 liter "Diaion" HP-20 column (washed with methanol and pre-equilibrated with MeOH/H$_2$O 50:50) at a flow rate of 2-4 liters per minute. The resin was then washed with 567 liters MeOH/H$_2$O 65:35 and eluted with 454 liters 100% MeOH.

The HP-20 cut rich in Compound I was concentrated to a volume of 6 liters, via first dilution with H$_2$O and then adsorbing and eluting from smaller HP-20 column (10 liters) in a manner similar to that employed in the larger HP 20 column.

Two liters (of a total of 6 liters) of the concentrated HP-20 rich cut was diluted with 2 liters of water and charged to a 800A Preparative HPLC system (Separations Technology) equipped with a 3.9 liter C18 column (Amicon) pre-washed with MeOH and preequilibrated with MeOH/H$_2$O 50:50. The charge was followed by 500 milliliters of MeOH/H$_2$O 50:50 and eluted at a flow rate of 212 ml/min with a linear gradient from MeOH/H$_2$O 50:50 to 100 percent MeOH in a 60 minute time periOd Fractions were analyzed via HPLC, combined and concentrated to dryness to yield approximately 20 grams of Compound I of 88 percent purity.

EXAMPLE VI

From the 6-liter concentrate of HP-20 cut rich in Compound I obtained as described in Example V, 900 milliliters was taken for purification.

To 900 milliliters was added an equal volume of methanol and to the resulting solution was added 900 milliliters of water, 900 milliliters of hexane and 900 milliliters of isopropyl acetate and shaken vigorously. An inseparable emulsion resulted, here 450 milliliters of methanol was added to obtain two layers. The lower layer which amounted to 2.5 liters was added to 900 milliliters of hexane, 900 milliliters of isopropyl acetate and 450 milliliters of methanol and again shaken vigorously and a lower layers of 3 liters was recovered. The partition step was performed a third time on the lower layer to generate another lower layer amounting to 3 liters.

The final lower layer from the partitioning experiments was concentrated to dryness. The residue (4 grams) was added to 50 milliliters of a mixture of CH$_2$Cl$_2$/CH$_3$OH/5%CH$_3$COOH (72.5/27.5/10) whereupon it was dissolved in the lower layer. This solution was chromatographed in 2 liters of silica gel 60 (230-400 mesh) at 50 ml/min using the same CH$_2$Cl$_2$/CH$_3$OH/ 5%CH3COOH (72.5/27.5/10) (72.5/27.5/10) as the mobile phase to obtain Compound 1 of high purity separated from minor components.

EXAMPLE VII 1000 compressed tablets each containing milligrams of Compound I are prepared from the following formulation:

| | Grams |
|---|---|
| Compound I | 500 |
| Starch | 750 |
| Dibasic calcium phosphate hydrous | 5000 |
| Calcium stearate | 2.5 |

The finely powdered ingredients are mixed well and granulated with 10 percent starch paste. The granulation is dried and compressed into tablets.

EXAMPLE VIII 1000 hard gelatin capsules, each containing 210 milligrams of Compound IA are prepared form the following formulation:

| Compound | Grams |
|---|---|
| Compound I | 500 |
| Starch | 250 |
| Lactose | 750 |
| Talc | 250 |

-continued

| Compound | Grams |
| --- | --- |
| Calcium stearate | 10 |

A uniform mixture of the ingredients is prepared by blending and used to fill two-piece hard gelatin capsules.

EXAMPLE IX

An ointment suitable for topical application may be prepared by intimately dispersing 13 milligrams of Compound I in 1 gram of commercially available polyethylene/hydrocarbon gel.

EXAMPLE X

An injectable suspension (IM) may be prepared as follows:

|  | mg/ml |
| --- | --- |
| Compound I | 10.0 |
| Methylcellulose | 5.0 |
| Tween 80 | 0.5 |
| Benzyl alcohol | 9.0 |
| Benzalkonium chloride | 1.0 |
| Water | to 1 ml |

EXAMPLE XI

An aerosol composition may be prepared having the following formulation:

|  | Per Canister |
| --- | --- |
| Compound I | 24 mg |
| Lecithin NF liquid concentrate | 1.2 mg |
| Trichlorofluoromethane | 4.025 g |
| Dichlorodifluoromethane | 12.15 g |

What is claimed:

1. A method for enhancing the production of compound having the formula

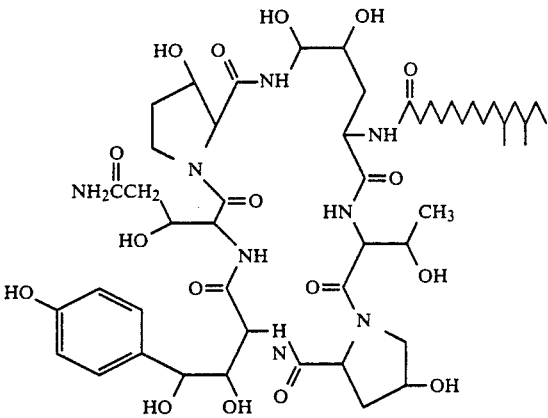

which comprises cultivating *Zalerion arboricola* ATCC 20868 in a nutrient medium containing mannitol as the primary source of carbon.

2. A method for producing the compound of formula (I) in Claim 1 in increased yield which comprises cultivating *Z. arboricola* in an aqueous nutrient medium which contains
   (1) a carbon source comprising mannitol
   (2) a nitrogen source comprising a milk protein hydrolysate, and
   (3) a buffer comprising glycine or an inorganic phosphate 3. A method according to claim 2 wherein the nutrient medium employed also contains trace elements and lactic acid.

4. A method according to claim 3 wherein the nutrient medium employed contains, in addition, a vegetable oil selected from soy, peanut or sunflower oils.

5. A method according to claim 2 wherein the nutrient medium is of the following composition in grams per liter: D-mannitol, 20–100; $KH_2PO_4$, 0.5–3; glycine, 1–4; peptonized milk, 2–20; lactic acid, 0–3; trace elements solution, 0–15 ml; vegetable oil, 0–20.

6. A method for producing the compounds of formula I in claim 1 at an increased rate of production of the compound which comprises cultivating *Z. arboricola* in nutrient medium which contains mannitol in an amount of at least 4 percent by weight and maintaining pH at about 5.5.

* * * * *